United States Patent [19]

Imatani et al.

[11] Patent Number: 4,958,002
[45] Date of Patent: Sep. 18, 1990

[54] HIGH PURITY CRYSTALS OF BIPHENYLTETRACARBOXYLIC DIANHYDRIDE AND PROCESS FOR THEIR PREPARATION

[75] Inventors: Katsuo Imatani; Shinichirou Yamamoto; Genji Koga, all of Ube, Japan

[73] Assignee: Ube Industries, Ltd., Ube, Japan

[21] Appl. No.: 211,815

[22] Filed: Jun. 27, 1988

[30] Foreign Application Priority Data

Jun. 25, 1987 [JP] Japan .................. 62-159246

[51] Int. Cl.$^5$ ..................... C08G 69/26; C07D 307/77
[52] U.S. Cl. ..................... 528/353; 528/170; 528/172; 549/241
[58] Field of Search ............ 528/353, 170, 172; 549/241

[56] References Cited

FOREIGN PATENT DOCUMENTS 57-15098  3/1982  Japan .

*Primary Examiner*—John Kight, III
*Assistant Examiner*—P. Hampton-Hightower
*Attorney, Agent, or Firm*—Frishauf, Holtz, Goodman & Woodward

[57] ABSTRACT

High purity crystals of a biphenyltetracarboxylic dianhydride produced by dehydration of a biphenyltetracarboxylic acid, which contain almost no biphenyltricarboxylic acid or its anhydride, or a small amount such as an amount of not more than 0.2 wt. %, are of value to produce an aromatic polyamic acid or polyimide having an increased high molecular weight. The high purity crystals of a biphenyltetracarboxylic dianhydride can be prepared from a biphenyltetracarboxylic acid by a dehydration process wherein the biphenyltetracarboxylic acid is heated under carefully controlled conditions.

13 Claims, No Drawings

HIGH PURITY CRYSTALS OF BIPHENYLTETRACARBOXYLIC DIANHYDRIDE AND PROCESS FOR THEIR PREPARATION

FIELD OF THE INVENTION

The present invention relates to high purity crystals of biphenyltetracarboxylic dianhydride, a process for the preparation of the high purity crystals from crystals of biphenyltetracarboxylic acid, and a process for the preparation of an aromatic polyamic acid or polyimide using the high purity crystals of a biphenyltetracarboxylic dianhydride.

BACKGROUND OF THE INVENTION

An aromatic polyimide is very excellent as a heat-resistant resin, and it is well known that the aromatic polyimide can be advantageously prepared in industry using a biphenyltetracarboxylic dianhydride and an aromatic diamine as starting materials, and possibly via production of a polyamic acid. The polyamic acid can be converted into a polyimide through imdation.

The biphenyltetracarboxylic dianhydride can be obtained by a process comprising the steps of dimerizing a phthalic acid diester such as dimethyl o-phthalate in the presence of a palladium catalyst, then subjecting the resulting dimer to various treatments such as purification, crystallization and hydrolysis to prepare a biphenyltetracarboxylic acid, and subsequently heating the biphenyltetracarboxylic acid for dehydration at a high temperature.

As for dehydration of the biphenyltetracarboxylic acid under heating at a high temperature, Japanese Patent Publication No. 57(1982)-15098 describes, for example, a method of heating the biphenyltetracarboxylic acid at a temperature of 100° to 500° C. in a nitrogen gas atmosphere under atmospheric pressure or reduced pressure such as a pressure of not lower than 40 mmHg to dehydrate the biphenyltetracarboxylic acid.

It has been found by the present inventors that the conventional method can hardly give a satisfactorily pure biphenyltetracarboxylic dianhydride. In more detail, when a biphenyltetracarboxylic dianhydride obtained by the conventional method is polymerized with an aromatic diamine to prepare an aromatic polyamic acid or polyimide, the viscosity of the aromatic polyamic acid or polyimide produced in the polymerization reaction liquid does not become sufficiently high. This means that an aromatic polyimide having a satisfactorily high molecular weight cannot be obtained.

The inventors have made study for discovering the reason why the viscosity of the polyamic acid or polyimide produced in the reaction liquid does not increase satisfactorily when the biphenyltetracarboxylic dianhydride obtained by the conventional method is used for the polymerization with an aromatic diamine. As a result, it has been found that increase of content of a biphenyltricarboxylic acid or its anhydride which is produced in the reaction and emigrates into the reaction product (i.e., biphenyltetracarboxylic dianhydride in the form of crystals) as impurity disturbs increase of the viscosity of the aromatic polyamic acid or polyimide produced in the polymerization reaction. Thus, it has been concluded that the biphenyltricarboxylic acid or its anhydride having emigrated into the crystals of a biphenyltetracarboxylic dianhydride disturbs production of an aromatic polyamic acid or polyimide having a satisfactorily high molecular weight.

Based on the above-mentioned finding, the present inventors have studied a process for preparing a high purity biphenyltetracarboxylic dianhydride which is almost free from contamination of a biphenyltricarboxylic acid or its anhydride. As a result of the study, the present inventors have discovered that crystals of a biphenyltetracarboxylic dianhydride containing almost no biphenyltricarboxylic acid or its anhydride, or containing an extremely small amount such as an amount of not more than 0.2 wt. %, can be obtained by heating crystals of a biphenyltetracarboxylic acid for dehydration under the specifically controlled heating conditions. The present inventors have also discovered that the employment of the above-obtained crystals of a biphenyltetracarboxylic dianhydride containing almost no biphenyltricarboxylic acid or its anhydride makes it possible to prepare an aromatic polyamic acid or polyimide having an increased high molecular weight.

SUMMARY OF THE INVENTION

It is an object of the present invention to provide high purity crystals of a biphenyltetracarboxylic dianhydride which are of value as one of the starting monomers for preparing a high molecular weight aromatic polyamic acid or polyimide and to provide an industrially advantageous process for preparing the high purity biphenyltetracarboxylic dianhydride crystals.

There is provided by the present invention high purity crystals of a biphenyltetracarboxylic dianhydride produced by dehydration of crystals of a biphenyltetracarboxylic acid, which contains a biphenyltricarboxylic acid or its anhydride in an amount of not more than 0.2 wt. %.

The high purity crystals of a biphenyltetracarboxylic dianhydride can be advantageously prepared by a specifically controlled process of heating crystals of a biphenyltetracarboxylic acid for dehydration to a dehydration temperature of not lower than 250° C. in an inert gas atmosphere. The heating process comprises the step of preliminarily heating the crystals of a biphenyltetracarboxylic acid from 80° C. to the dehydration temperature at an average rate of temperature rise of not more than 50° C./hour to remove water deposited on the crystals and water of crystallization from the crystals, and the step of subsequently heating said crystals for dehydration at a dehydration temperature in the range of 250° to 300° C. for at least 3 hours.

The high purity crystals of a biphenyltetracarboxylic dianhydride of the invention contain an impurity of a biphenyltricarboxylic acid or its anhydride in only an extremely small amount. In the case where these crystals are used for copolymerization with an aromatic diamine, the viscosity of the resulting aromatic polyamic acid or polyimide in the polymerization reaction liquid reaches a satisfactorily high degree. This means that an aromatic polyamic acid or polyimide of an increased high molecular weight can be obtained.

DETAILED DESCRIPTION OF THE INVENTION

The high purity crystals of a biphenyltetracarboxylic dianhydride of the present invention are prepared from crystals of a biphenyltetracarboxylic acid.

The crystals of a biphenyltetracarboxylic acid can be prepared by dimerization of a di(lower)alkylester of o-phthalic acid such as dimethyl o-phthalate and then hydrolyzing the resulting dimer.

The biphenyltetracarboxylic acid given by dimerization of di(lower)alkyl ester of o-phthalic acid generally is a mixture of three isomers such as 3,3',4,4'-biphenyltetracarboxylic acid, 2,2',3,3'-biphenyltetracarboxylic acid and 2,3,3',4'-biphenyltetracarboxylic acid. Generally, the mixture is then treated for isolation of one of these isomers from others. Advantageously employable in the invention is 3,3',4,4'-biphenyltetracarboxylic acid.

In the process of the invention for dehydration of crystals of a biphenyltetracarboxylic acid, a step of preheat treatment of crystals of a biphenyltetracarboxylic acid in which temperature of the crystals is raised from approx. 80° C. to a dehydration temperature is performed at an average rate of temperature rise of not more than 50° C./hour, preferably not more than 45° C./hour, generally for a period of not longer than 20 hours, preferably not longer than 15 hours, to remove water deposited on the crystals and water of crystallization from the crystals.

The preheat treatment of the biphenyltetracarboxylic acid crystals preferably comprises the following two steps: that is, a first step of heating the crystals of a biphenyltetracarboxylic acid at temperatures rising from approx. 80° C. to approx. 130° C. at an average rate of temperature rise of not more than 30° C./hour, preferably 0.01° to 28° C./hour, for a period of generally not less than 0.5 hour, preferably 1 to 5 hours, to remove mainly water deposited on the crystals; and a second step of heating the crystals of a biphenyltetracarboxylic acid at temperatures rising from approx. 130° C. to the dehydration temperature at an average rate of temperature rise of not more than 50° C./hour, preferably 10° to 45° C./hour, for a period of generally not less than 0.5 hour, preferably 1 to 6 hours, to remove mainly water of crystallization from the crystals.

The above-mentioned preheat treatment is performed to efficiently dehydrate the crystals of a biphenyltetracarboxylic acid in the subsequent dehydration step.

In more detail, in the first step of the preheat treatment, the deposited water which is kept or adsorbed within voids of the crystals is gradually removed through evaporation during the rise of temperature from approx. 80° to 130° C., and the crystals are sufficiently dried. In the second step of the preheat treatment, water of crystallization which is positioned within the crystals or bonded to the crystals by intermolecular force between the crystal molecule and the water molecule is gradually removed from the crystals during the rise of temperature from approx. 130 to the dehydration temperature. As a result, water which is an obstacle in the dehydration, is almost completely removed and the crystals are thoroughly dried.

If the preheat treatment for heating the biphenyltetracarboxylic acid at temperatures rising from approx. 80° C. to the dehydration temperature is performed at an average rate of temperature rise of more than 50° C./hour, the deposited water and the water of crystallization are insufficiently removed from the crystal (that is, the crystals are insufficiently dried), and hence the temperature of the subsequent heat treatment for dehydration can be hardly kept uniformly over the crystals. When the dehydration temperature is not uniform over the crystals, the crystals are heated non-uniformly and hence the crystals are forced to locally have an extremely high temperature. Otherwise, the crystals tend to sinter. When the sintering takes place, the removal of water is done incompletely and the dehydration of the crystals is made nonuniformly. Further, a biphenyltricarboxylic acid or its anhydride (which is a side reaction product) is easily produced owing to decarboxylation.

The second step in the preheat treatment may comprise continuous two stages. For example, the first half (namely, the temperature rise from approx. 130° C. to approx. 170° C.) of the second step is carried out at an average rate of temperature rise of not more than approx. 40° C./hour for at least 0.5 hour, and the latter half (namely, the temperature rise from approx. 170° C. to the dehydration temperature) of the second step is carried out at an average rate of temperature rise of not more than approx. 50° C./hour.

The crystals having been subjected to the above-mentioned preheat treatment are subsequently heated for dehydration under the following conditions:

(1) atmosphere: an inert gas atmosphere in which an active gas such as oxygen is not contained, preferably a nitrogen gas atmosphere;

(2) pressure: atmospheric pressure or a reduced pressure, preferably atmospheric pressure or a reduced pressure of not lower than 40 mmHg;

(3) temperature: 250° to 300° C., preferably 255° to 290° C.; and (4) period of time: at least 3 hours, preferably 5 to 40 hours, more preferably 10 to 30 hours.

If desired, the above-mentioned heating for dehydration may be performed under stirring.

According to the present invention, the crystals of a biphenyltetracarboxylic acid of which water content has been sufficiently reduced in the aforementioned preheat treatment are then heated for dehydration, whereby one molecule of water is eliminated from a pair of adjacent carboxyl groups of the biphenyltetracarboxylic acid to form an anhydride ring having carboxyl groups. Thus, the desired dehydration reaction is performed. As a result, a biphenyltetracarboxylic dianhydride is produced. In this procedure, production of by-products such as a biphenyltricarboxylic acid or its anhydride (e.g., 3,3',4-biphenyltricarboxylic acid, 3,4,4'-biphenyltricarboxylic acid and anhydrides thereof) is suppressed because the dehydration reaction proceeds uniformly over the crystals of a biphenyltetracarboxylic acid. Further, most of the by-product is eliminated from the crystals of the resulting biphenyltetracarboxylic dianhydride through sublimation.

In the preheat treatment and the heat treatment for dehydration, the biphenyltetracarboxylic acid crystals can be heated using an appropriate heating medium such as pressurized steam or other heating medium which is introduced into a space provided inside of a rotary paddle of a stirring device or a jacket provided around an outer wall of a reaction vessel. In the case of using pressurized steam and other heating medium both as heat source, the jacket around the reaction vessel and the space inside of the rotary paddle are preferably introduced with different heating medium from each other.

For the preheat treatment, it is preferred to use pressurized steam. The pressure of steam employed in the first step of the preheat treatment preferably is in the range of 1.0 to 5 kg/cm², more preferably in the range of 1.1 to 3 kg/cm².

For the heat treatment for dehydration, it is preferred to use a heat-resistant heating medium such as liquid or vapor of an aromatic compound (e.g., alkylbenzene, alkylnaphthalene, alkyldiphenyl, diphenyl ether, hydrogenated triphenyl or dibenzyltoluene) or a mineral oils (e.g., paraffinic mineral oil or alkylaromatic mineral oil).

The use of the same kinds of heat-resistant heating media having different temperatures for the preheat treatment and the dehydration heat treatment is advantageous. For example, the rise of temperature can be made continuously or by stages in each heating procedure. Further, it is unnecessary to separately supply different heating media into each of the aimed parts of the reaction vessel (e.g., a space within the rotary paddle of the stirring device or a jacket provided around the reaction vessel). Thus, a complicated operation is not necessary.

As the heat source, any heat source can be employed in the invention, provided that uniform heating can be made in each heating procedure and that the rate of temperature rise is controlled within the specific range of the invention. For example, there can be used electric energy source such as an electrical resistance heater and an infrared heater.

The biphenyltetracarboxylic dianhydride crystals produced as above contain a biphenyltricarboxylic acid or its anhydride in an amount of not more than 0.2 wt. % of the whole amount of the crystals. The amount of biphenyltricarboxylic acid and its anhydride can be reduced to less than 0.15 wt. % and further to less than 0.1 wt. % by appropriately selecting the dehydration conditions. In the case of polymerizing such high purity biphenyltetracarboxylic dianhydride crystals with an aromatic diamine in the conventional manner, the viscosity of an aromatic polyamic acid or polyimide produced in the polymerization reaction liquid can be increased, and an aromatic polyamic acid or polyimide having a very high molecular weight can be obtained.

The relative viscosity of the aromatic polyamic acid or polyimide contained in the reaction liquid is generally expressed by a logarithmic viscosity (logarithmic viscosity number). The logarithmic viscosity is determined by the following equation:

$$\text{Logarithmic viscosity} = \frac{\text{natural log. (polymer soln. viscosity/solvent viscosity)}}{\text{solution concentration}}$$

The logarithmic viscosity of the aromatic polyamic acid or polyimide has a good correlation with a molecular weight thereof.

An aromatic polyamic acid prepared from a biphenyltetracarboxylic dianhydride and an aromatic diamine preferably has a logarithmic viscosity in the range of 2.5 to 7.0, more preferably in the range of 3.0 to 5.0, (temperature: 30° C., polymer concentration: 0.5 g/100 ml-solvent, solvent: N-methyl-2-pyrrolidone). An aromatic polyamic acid having such a high logarithmic viscosity can be easily obtained using the biphenyltetracarboxylic dianhydride containing almost no biphenyltricarboxylic acid or its anhydride.

The present invention is further illustrated by the following examples.

EXAMPLE 1

280 kg. of pure 3,3',4,4'-biphenyltetracarboxylic acid crystals were charged into a reaction vessel equipped therein with a disc-shaped stirring device with a rotary paddle having a horizontal axis and having a space therein for introducing pressurized steam or a heat-resistant heating medium and provided with a jacket for introducing pressurized steam or a heat-resistant heating medium around the outer wall.

The 3,3',4,4'-biphenyltetracarboxylic acid crystals in the vessel were heated up to 100° C. at an average rate of temperature rise of 30° C./hour in a nitrogen gas atmosphere at atmospheric pressure under stirring by introducing steam 2 kg/cm²G into both of the space of the rotary paddle and the jacket, and then the temperature of the crystals was kept at 100° C. for approx. 1 hour, to remove the deposited water from the crystals (first step of the preheat treatment).

Subsequently, the crystals were further heated from 100° to 130° C. at an average rate of temperature rise of 25° C./hour in a nitrogen atmosphere at atmospheric pressure under stirring by changing the pressure of steam in both of the spaces of the rotary paddle and the jacket to 6 kg/cm²G, and then the temperature of the crystals was kept at 130° C. for approx. 2 hours, to remove the water of crystallization from the crystals (second step of the preheat treatment).

The crystals having been subjected to the preheat treatment were then heated to reach temperature of 280° C. at an average rate of temperature rise of 35° C./hour and then further heated at 280° C. for 20 hours in a nitrogen atmosphere under stirring, for performing dehydration. Thus, 247 kg. of crystals of 3,3'4,4'-biphenyltetracarboxylic dianhydride were produced.

Into a 300 ml-volume three-necked flask equipped with a stirrer and a nitrogen-blowing tube were charged 11.76 g. of the crystals of biphenyltetracarboxylic dianhydride obtained as above, 8.00 g. of diaminodiphenyl ether and 177.84 g. of N-methyl-2-pyrrolidone, and they were stirred at 30° C. for 5.5 hours in a nitrogen atmosphere to prepare an aromatic polyamic acid in a polymerization reaction liquid.

The viscosity of the aromatic polyamic acid produced in the reaction liquid was measured, and the logarithmic viscosity of the aromatic polyamic acid was determined according to the aforementioned equation.

The result of the dehydration and the determined logarithmic viscosity are set forth in Table 1.

EXAMPLE 2

The procedures for preparing crystals of 3,3',4,4'-biphenyltetracarboxylic dianhydride in Example 1 were repeated except for introducing only one kind of heat-resistant heating medium having various temperatures into both of the jacket and the space of the rotary paddle, and performing the preheat treatment and the heat treatment for dehydration as follows.

In the first step of the preheat treatment, the crystals were heated up to approx. 100° C. at an average rate of temperature rise of 25° C./hour and then the temperature of the crystals was kept at 100° C. for 1 hour, to remove the deposited water from the crystals.

In the first half of the second step of the preheat treatment, the crystals were heated from 100° to 150° C. at an average rate of temperature rise of 25° C./hour and the temperature of the crystals was kept at 150° C. for 2 hours, and in the latter half of the second step of the preheat treatment, the crystals were heated from 150° to 280° C. (dehydration temperature) at an average rate of temperature rise of 35° C./hour, to remove the water of crystallization from the crystals.

Then, the heat treatment for dehydration was performed keeping the temperature of the crystals at 280° C. for 20 hours, to dehydrate 3,3',4,4'-biphenyltetracarboxylic acid.

Thus, 247 kg. of crystals of 3,3',4,4'-biphenyltetracarboxylic dianhydride were prepared.

Using the obtained biphenyltetracarboxylic dianhydride, an aromatic polyamic acid was produced in the same manner as described in Example 1. Further, the logarithmic viscosity of the aromatic polyamic acid produced in the reaction liquid was determined according to the aforementioned equation.

The result of the dehydration and the determined logarithmic viscosity are set forth in Table 1.

EXAMPLE 3

The procedures for preparing crystals of 3,3',4,4'-biphenyltetracarboxylic dianhydride in Example 1 were repeated except for performing the preheat treatment and the heat treatment for dehydration as follows.

In the first step of the preheat treatment, the crystals were continuously heated up to approx. 130° C. at an average rate of temperature rise of 20° to 25° C./hour by the use of a heat-resistant heating medium.

In the second step of the preheat treatment, the crystals were heated continuously from 130° to 280° C. at an average rate of temperature rise of 30° to 35° C./hour by the use of a heat-resistant heating medium.

Then, the heat treatment for dehydration was performed keeping the temperature of the crystals at 280° C. for 20 hours, to dehydrate 3,3',4,4'-biphenyltetracarboxylic acid.

Thus, 247 kg. of crystals of 3,3',4,4'-biphenyltetracarboxylic dianhydride were prepared.

Using the obtained biphenyltetracarboxylic dianhydride, an aromatic polyamic acid was produced in the same manner as described in Example 1. Further, the logarithmic viscosity of the aromatic polyamic acid produced in the reaction liquid was determined according to the aforementioned equation.

The result of the dehydration and the determined logarithmic viscosity are set forth in Table 1.

COMPARISON EXAMPLE 1

Using the same reaction vessel and the starting material (crystals) as used in Example 1, the crystals were subjected to heat treatments by introducing a heat-resistant heating medium of a high temperature into the jacket and the space of the rotary paddle. In the heat treatments, the temperature rise of the crystals up to 280° C. was carried out at one stage for 2 hours (average rate of temperature rise: 100° C./hour), and then the temperature of the crystals was kept at 280° C. for 5 hours. Other conditions than the above-mentioned ones were the same as those of Example 1. Thus, the crystals of 3,3',4,4'-biphenyltetracarboxylic acid were dehydrated to prepare 237 kg. of crystals of 3,3',4,4'-biphenyltetracarboxylic dianhydride.

Using the obtained crystals of biphenyltetracarboxylic dianhydride, an aromatic polyamic acid was produced in the same manner as described in Example 1. Further, the logarithmic viscosity of the aromatic polyamic acid produced in the reaction liquid was determined according to the aforementioned equation.

The result of the dehydration and the determined logarithmic viscosity are set forth in Table 1.

TABLE 1

| | Whole Acid (%) | Dehydration Rate (%) | Tri-Acid (%) | Logarithmic Viscosity |
|---|---|---|---|---|
| Example 1 | 100 | 100 | 0.06 | 4.0 |
| Example 2 | 100 | 100 | 0.06 | 4.0 |
| Example 3 | 100 | 100 | 0.07 | 3.8 |
| Com. Ex. 1 | 99 | 99 | 0.3 | 2.3 |

The terms "whole acid", "dehydration rate", "tri-acid" and "logarithmic viscosity" expressed in Table 1 have the following meanings:

whole acid: ratio by weight of the amount of a biphenylcarboxylic acid component (in the form of dianhydride) to the whole amount of the dehydrated product;

dehydration rate: ratio of 3,3',4,4'-biphenyltetracarboxylic dianhydride to the amount of the introduced whole acid;

tri-acid: ratio by weight of biphenyltricarboxylic acid (and/or its anhydride) to the amount of the whole dianhydride; and logarithmic viscosity: value determined by the following equation under the conditions of a measuring temperature of 30° C., polymer concentration of 0.5 g/100 ml-solvent (N-methyl-2-pyrrolidone).

$$\text{Logarithmic viscosity} = \frac{\text{natural log. (polymer soln. viscosity/solvent viscosity)}}{\text{solution concentration}}$$

We claim:

1. Crystals of a biphenyltetracarboxylic dianhydride produced by dehydration of a biphenyltetracarboxylic acid, which contains a biphenyltricarboxylic acid or its anhydride in an amount of not more than 0.2 wt. %.

2. The crystals of a biphenyltetracarboxylic dianhydride as claimed in claim 1, wherein the content of said biphenyltricarboxylic acid or its anhydride is less than 0.15 wt. %.

3. The crystals of a biphenyltetracarboxylic dianhydride as claimed in claim 1, wherein the content of said biphenyltricarboxylic acid or its anhydride is less than 0.10 wt. %.

4. In a process for the preparation of a biphenyltetracarboxylic dianhydride by heating crystals of a biphenyltetracarboxylic acid to a dehydration temperature of not lower than 250° C. in an inert gas atmosphere to dehydrate said acid and form said dianhydride, the improvement which comprises the steps of:
preliminarily heating the crystals of a biphenyltetracarboxylic acid containing adsorbed water and water of crystallization from 80° C. to the dehydration temperature at an average rate of temperature rise of not more than 50° C./hour to remove adsorbed water and water of crystallization from the crystals; and
subsequently heating said crystals at a dehydration temperature in the range of 250° to 300° C. for at least 3 hours to dehydrate said acid and form said dianhydride.

5. The process as claimed in claim 4, wherein said step of preliminary heating comprises the steps of:
heating the crystals of a biphenyltetracarboxylic acid to 130° C. at an average rate of temperature rise of not more than 30° C./hour to remove mainly adsorbed water; and subsequently heating said crystals of a biphenyltetracarboxylic acid from 130° C. to the dehydration temperature at an average rate of temperature rise of not more than 50° C./hour to remove mainly water of crystallization from the crystals.

6. The process as claimed in claim 4, wherein said step of preliminary heating and the step of subsequent heating are performed continuously.

7. In a process for the preparation of an aromatic polyamic acid or polyimide by polymerizing a biphenyltetracarboxylic dianhydride and an aromatic diamine, the improvement wherein crystals of a biphenyltetracarboxylic dianhydride produced by dehydration of a biphenyltetracarboxylic acid which contains a biphenyltricarboxylic acid or its anhydride in an amount of not more than 0.2 wt. % are used as the biphenyltetracarboxylic dianhydride.

8. The process as claimed in claim 7, wherein the content of the biphenyltricarboxylic acid or its anhydride is less than 0.15 wt. %.

9. The process as claimed in claim 7, wherein the content of the biphenyltricarboxylic acid or its anhydride is less than 0.10 wt. %.

10. The process as claimed in claim 7, wherein said crystals of a biphenyltetracarboxylic anhydride have been prepared by a process which comprises the step of preliminarily heating crystals of a biphenyltetracarboxylic acid from 80° C. to its dehydration temperature at an average rate of temperature rise of not more than 50° C./hour to remove adsorbed water and water of crystallization from the crystals, and the step of subsequently heating said crystals at a dehydration temperature in the range of 250° to 300° C. for at least 3 hours to dehydrate said acid and form said dianhydride.

11. The crystals of a biphenyltetracarboxylic dianhydride as claimed in claim 1, wherein said crystals form a polyamic acid having a logarithmic viscosity in the range of 2.5 to 7.0 when said crystals are reacted with diaminodiphenyl ether in N-methyl-2-pyrrolidone at 30° C. for 5.5 hours, said logarithmic viscosity being expressed in terms of a value measured in N-methyl-2-pyrrolidone at 30° C. and at a concentration of 0.5 g/100 ml of N-methyl-2-pyrrolidone.

12. The crystals of a biphenyltetracarboxylic dianhydride as claimed in claim 11, wherein said logarithmic viscosity is in the range of 3.0 to 5.0.

13. Crystals of a biphenyltetracarboxylic dianhydride produced by the process of claim 4 and which contain a diphenyltricarboxylic acid or its anhydride in an amount of not more than 0.2 wt. %.

* * * * *